(12) United States Patent
Bartl

(10) Patent No.: US 8,026,388 B2
(45) Date of Patent: Sep. 27, 2011

(54) PROCESS FOR MAKING 1-HYDROXYALKYLIDENE-1,1-BIPHOSPHONIC ACIDS

(75) Inventor: Jiri Bartl, Strelice (CZ)

(73) Assignee: Synthon BV, Nijmegen (NL)

( * ) Notice: Subject to any disclaimer, the term of this patent is extended or adjusted under 35 U.S.C. 154(b) by 257 days.

(21) Appl. No.: 12/501,401

(22) Filed: Jul. 10, 2009

(65) Prior Publication Data

US 2010/0010258 A1    Jan. 14, 2010

Related U.S. Application Data

(60) Provisional application No. 61/080,107, filed on Jul. 11, 2008.

(51) Int. Cl.
*C07F 9/38* (2006.01)
(52) U.S. Cl. ........... 562/13; 562/22; 564/15; 546/22; 546/23; 548/112; 548/113
(58) Field of Classification Search ........... 546/22, 546/23; 548/112, 113; 562/13, 22; 564/15
See application file for complete search history.

(56) References Cited

U.S. PATENT DOCUMENTS

| | | | |
|---|---|---|---|
| 4,407,761 A | 10/1983 | Blum et al. | |
| 4,922,007 A | 5/1990 | Kieczykowski et al. | |
| 5,019,651 A | 5/1991 | Kieczykowski | |
| 5,510,517 A | 4/1996 | Dauer et al. | |
| 5,908,959 A | 6/1999 | Kubela et al. | |
| 7,038,083 B2 | 5/2006 | Lidor-Hadas et al. | |
| 2006/0258625 A1 | 11/2006 | Deshpande et al. | |

FOREIGN PATENT DOCUMENTS

| | | |
|---|---|---|
| WO | WO 98/34940 | 8/1998 |
| WO | WO 02/090367 | 11/2002 |
| WO | WO 2007/083240 | 7/2007 |

*Primary Examiner* — Peter O Sullivan
(74) *Attorney, Agent, or Firm* — Muncy, Geissler, Olds & Lowe, PLLC

(57) ABSTRACT

Synthesis of biphosphonate compounds can be advantageously carried out in a solvent/diluent comprising a compound of formula (3)

$$\underset{R_2}{\overset{R}{\diagdown}}\underset{OR_1}{\overset{OR_1}{\diagup}}C \qquad (3)$$

wherein R is hydrogen or a C1-C6 alkyl group; each of R1 is a C1-C6 alkyl group or both R1 groups are linked to form a C1-C3 alkylene group; and R2 is hydrogen, a C1-C6 alkyl group, a C1-C6 alkoxy group, or is linked together with R to form a C3-C7 carbon ring.

13 Claims, No Drawings

PROCESS FOR MAKING 1-HYDROXYALKYLIDENE-1,1-BIPHOSPHONIC ACIDS

This application claims the benefit of priority under 35 U.S.C. §119(e) from U.S. provisional application Ser. No. 61/080,107, filed Jul. 11, 2008, the entire contents of which are incorporated herein by reference.

BACKGROUND OF THE INVENTION 1-hydroxyalkylidene-1,1-biphosphonic acids of the general formula (1)

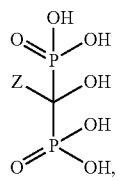
(1)

including salts and hydrates thereof, represent an important class of pharmaceuticals, useful for treatment or prevention of osteoporosis. In the general formula (1), the Z represents a methyl group or a substituted methyl group, particularly substituted by a nitrogen-containing substituent. More particularly, the biphosphonic acids listed below have been the subject of considerable research efforts and many of them are marketed as pharmaceutically active compounds in various pharmaceutical compositions, mostly as hydrated sodium salts:

| | |
|---|---|
| etidronic acid | Z = methyl |
| pamidronic acid | Z = 2-aminoethyl |
| alendronic acid | Z = 3-aminopropyl |
| neridronic acid | Z = 5-aminopentyl |
| olpadronic acid | Z = 2-(N,N-dimethylamino)ethyl |
| ibandronic acid | Z = 2-(N-methyl-N-pentylamino)ethyl |
| risedronic acid | Z = pyridin-3-ylmethyl |
| zoledronic acid | Z = 2-imidazol-1-ylmethyl |
| minodronic acid | Z = (imidazo[1,2a]pyridin-2yl)methyl |

In a known general process for making the compounds of formula (1), an acid of the general formula (2)

is reacted in a solvent (or in a diluent) and at an enhanced temperature with a phosphonation agent, which may be a mixture of phosphorous acid and a halophosphorous compound (such as phosphorous trichloride $PCl_3$, phosphorous pentachloride $PCl_5$, phosphorous oxychloride $POCl_3$, and the like), and the resulting complex mixture of cyclic pyrophosphonate intermediates (the nature of which has been suggested, e.g., in U.S. Pat. No. 5,510,517) is hydrolyzed by heating the mixture with water or a non-oxidizing aqueous acid to form a biphosphonic acid. The obtained biphosphonic acid is then optionally isolated, or is optionally converted into a corresponding salt and then isolated.

There are many prior art documents dealing with this general process. Many of the used diluents do not fully dissolve the reaction components (e.g., the compound of formula (2) and/or the phosphonation agent), so that the resulting reaction mixture is a poorly stirred polyphasic mass, the work-up of which is quite complicated. See, e.g., U.S. Pat. No. 4,407,761, wherein the reaction proceeds in chlorobenzene, U.S. Pat. No. 7,038,083, wherein the diluent is an aromatic hydrocarbon, US 2006/0258625, which used diphenyl ether, or WO 2007/083240, which used a phenolic compound as a diluent. Solubilization may be achieved in some cases by using methane sulfonic acid (U.S. Pat. No. 4,922,007 and U.S. Pat. No. 5,019,651), polyalkylene glycols (U.S. Pat. No. 5,908,959, WO 98/34940), triglycerides or alkyl/aralkyl ethoxylates (WO 02/090367), however, these solubilization agents complicate the elaboration of the reaction mixture as well.

In general, the main problems in the known synthetic process are high viscosity and, in some embodiments, polyphasic character of the reaction mixture comprising the cyclic pyrophosphonate intermediates which leads to poor heat transfer and problems with subsequent work-up; use of high boiling solvents/diluents that may be difficult to remove from the reaction mixture or from the isolated product; and formation of side products arising from the excess of the phosphonation agents. These disadvantages are manifested, in particular, in a large scale production.

Thus, there is a need to improve the conditions of reaction between the compound of formula (2) and the phosphonation agent yielding the biphosphonates of the formula (1). In particular, there is a need to find a solvent/diluent, which is readily available, does not cause solidification of the reaction mixture, and can be easily removed from the product.

SUMMARY OF THE INVENTION

The present invention provides a simple and effective process for the preparation of biphosphonates especially of the formula (1), including salts and hydrates thereof, that can provide high purity and commercial scale.

A first aspect of the present invention relates to a process of making a compound of formula (1),

(1)

wherein Z is a C1-C6 alkyl group optionally substituted by an amino group, one or two C1-C6 alkylamino group(s), or a nitrogen-containing heterocyclic group, and salts and hydrates thereof, which comprises:

reacting in a solvent/diluent a carboxylic acid compound of formula (2) or a salt thereof

wherein Z is as defined above, with a phosphonation agent to form cyclic pyrophosphonate intermediates, wherein the solvent/diluent comprises at least one compound of formula (3)

(3)

wherein R is hydrogen or a C1-C6 alkyl group; each of R1 is a C1-C6 alkyl group or both R1 groups are linked to form a C1-C3 alkylene group; and R2 is hydrogen, a C1-C6 alkyl group, a C1-C6 alkoxy group, or is linked together with R to form a C3-C7 carbon ring; and hydrolyzing said cyclic pyrophosphonate intermediates to form a compound of formula (1) or a salt or hydrate thereof, wherein Z is as defined above.

Typically, the compound of formula (3) is an acetal (R2=H), a ketal (R2=C1-C6 alkyl or a C3-C7 ring together with R) or an ortho-ester (R2=O—R1). Preferably, the compound of formula (3) is a C1-C6 dialkyl acetal of formaldehyde (R=R2=H, R1=C1-C6 alkyl group), and more preferably is formaldehyde diethyl acetal $CH_2(OC_2H_5)_2$. Generally, the hydrolyzing step comprises contacting the cyclic pyrophosphonate intermediates with water, alcohol, or a mixture thereof. The process typically further comprises isolating the compound of formula (1) or a salt or hydrate thereof, such as by precipitation.

DETAILED DESCRIPTION OF THE INVENTION

The present invention provides an improvement in the process of making the compounds of formula (1)

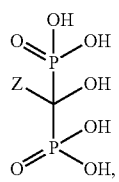
(1)

wherein Z is C1-C6 alkyl group optionally substituted by: an amino group, one or two C1-C6 alkylamino group(s), or a nitrogen-containing heterocyclic group (pyridinyl. imidazolyl, benzimidazolyl, imidazopyridinyl), by a reaction of an acid of formula (2)

Z—COOH (2), wherein Z is as defined above, and a phosphonation agent, which improvement is characterized by using an advantageous solvent/diluent system in which the reaction between the acid with the phosphonation agent takes place. The solvent/diluent system is of a low cost, low toxicity and easily available. By conducting the reaction in the solvent/diluent system of the present invention, the reaction mixture remains an easily stirred fluid, particularly a solution, thus allowing for good control of the reaction, easy upscaling, and simple isolation of product resulting in good yields and purity.

The solvent/diluent system of the present invention comprises at least one compound of the formula (3),

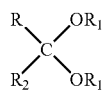
(3)

wherein R is hydrogen or a C1-C6 alkyl group; each of R1 is a C1-C6 alkyl group or both R1 groups are linked to form a C1-C3 alkylene group; and R2 is hydrogen, a C1-C6 alkyl group, a C1-C6 alkoxy group, or is linked together with R to form a C3-C7 carbon ring.

Typically, the solvent/diluent is chemically an acetal (R2=H), a ketal (R2=alkyl group or a C3-C7 ring together with R) or an ortho-ester (R2=O—R1). The solvent/diluent is advantageously a C1-C6 dialkyl acetal of formaldehyde (R=R2=H, R1=C1-C6 alkyl group). Examples of suitable solvents/diluents of the formula (3) include formaldehyde diethyl acetal (ethylal), dibutoxymethane (butylal), 1,3-dioxolan, propionaldehyde diethyl acetal, trimethyl orthoformate, and triethylorthoacetate. A preferred solvent/diluent of the formula (3) is formaldehyde diethyl acetal which can be represented as $CH_2(OC_2H_5)_2$.

A common feature of the compounds of the formula (3) is the presence of at least one geminal methylene-bisether linkage (—C—O—C—O—C—). Without wishing to be bound by any theory, it is believed that this particular arrangement of methylene and oxygen atoms in the molecule provides the enhanced solubilization properties vis-a-vis the starting materials and the reaction products, particularly the cyclic pyrophosphonate intermediates. The compound (3) also does not contain any reactive group, e.g., does not contain a carbonyl group, which may cause side reactions. Furthermore, the compounds of the formula (3) as defined above are, in general, volatile liquids that are removable from the reaction mixture, e.g., by distillation, without difficulties.

Advantageously, the compounds (3) are, in general, sensitive to aqueous or alcoholic acids; they may be hydrolyzed by water or alcohol in the presence of an acid under reactive conditions to components (aldehyde/ketone/ester R—CO—R2 and the alcohol R1—OH) that are even more volatile and/or miscible with water, so that even the trace amounts of them may be separated from the precipitated solid product. "Reactive conditions" are conditions necessary to decompose the cyclic pyrophosphonate intermediates to the desired acid (1). Moreover, the hydrolyzed components (aldehyde/ketone/ester R—CO—R2 and the alcohol R1—OH) may serve as antisolvents in the process of isolating the compound (1), which will be disclosed below.

The compounds of the formula (3) are obtainable by methods known in the art or are commercially available.

In a preferred mode, group Z in the acid of the formula (2) is the same as the group Z in the resulting biphosphonate. The acid (2) may be used in the process of the present invention also as a metal salt, e.g., sodium salt; any of the acids (2) that comprises a nitrogen-containing group Z may be used in the form of an acid addition salt thereof, e.g., as a hydrochloride. The compound (2) may also be used in its ester form.

More specifically, the groups Z in the compounds (1) and (2) are a C1-C6 alkyl group optionally substituted by an amino group, one or two C1-C6 alkylamino group(s), or a nitrogen-containing heterocyclic group (pyridinyl. imidazolyl, benzimidazolyl, imidazopyridinyl). The groups Z in the compounds (1) and (2) are typically represented by methyl, 2-aminoethyl, 3-aminopropyl, 5-aminopentyl, 2-(N, N-dimethylamino)ethyl, 2-(N-methyl-N-pentylamino)ethyl, pyridin-3-ylmethyl, 2-imidazol-1-ylmethyl, or (imidazo[1,2a]pyridin-2-yl)methyl, and include also precursors of these groups.

The acids of the formula (2) are obtainable by methods known in the art or are commercially available.

The reaction between the compound of the formula (2) defined above and the phosphonation agent in the solvent/diluent in the process of the present invention proceeds optimally at about 40° C. to 80° C., more preferably at 50-65° C.

The phosphonation agent is phosphorous acid and/or a halophosphorous compound, which is advantageously phosphorous trichloride $PCl_3$, phosphorous pentachloride $PCl_5$, phosphorous oxychloride $POCl_3$ and the like; and mixtures thereof. When the phosphonation agent is phosphorous acid and a halophosphorous compound the preferred molar ratio between the acid of the formula (2), phosphorous acid, and the halophosphorous compound is about 1:(1-5):(2-5), more preferably about 1:3-4:3-4.

The solvent/diluent comprising the compound of the formula (3) may be used in any suitable amount, which is advantageously 2 to 10 volumes based on weight of the acid of the formula (2) (i.e., 2-10 ml/mg). Optionally, an inert co-solvent/co-diluent may be added to the reaction mixture, such as an aromatic hydrocarbon or a polyalkyleneglycol.

After the completion of the phosphonation reaction (i.e., the reaction in the solvent/diluent comprising compound (3) of the compound (2) and the phosphonation agent), which may be monitored by a suitable analytical technique, e.g., a TLC or HPLC, the reaction mixture (or, alternatively, the isolated mixture of cyclic pyrophosphonate intermediates) is subjected to a hydrolytic and/or solvolytic reaction by contacting the reaction mixture with water and/or an alcohol. In this reaction, various reagents, particularly the halophosphorous compounds, and the compound of the formula (3) are decomposed as well. Advantageously, the above mixture of intermediates is treated by water, preferably at an enhanced temperature (advantageously higher than 60° C. including reflux temperature) and for a prolonged time (e.g., for at least 4 hours and preferably for at least 10 hours). A homogeneous organic/aqueous mixture is generally formed after the hydrolysis, wherein the product of the formula (1) stays dissolved in the mixture. Alternately, the reaction mixture is solvolyzed by an alcohol. Here, the volatile components are removed by evaporation and the reaction remainder is treated with water to hydrolyze the so-formed esters of the compounds of the formula (1) to the desired acid. The reaction mixture may also be treated with a mixture of water and alcohol.

The acid of the formula (1) may be isolated from the reaction mixture after hydrolysis in solid state by a suitable precipitation process. Advantageously, the reaction mixture, or if biphasic, the aqueous phase thereof, is neutralized and/or alkalinized by a molar equivalent or a slight molar excess of an alkali (e.g., sodium/potassium hydroxide or carbonate) to a pH of between 4 and 5, preferably between 4.2 and 4.5. The biphosphonic acid (1) is isolated from the aqueous phase as a solid monovalent alkali metal (monosodium or monopotassium) salt by precipitation thereof after adding a water miscible organic liquid (an antisolvent) such as an aliphatic alcohol in which the salt is less soluble. Preferably the amount of the antisolvent is about 0.8 to 2 volume equivalents to the volume of the water; higher amount of the antisolvent may cause co-precipitation of inorganic alkali metal salts as well, although these co-precipitated salts may be removed later in a purification step. The precipitated solid product is filtered from the liquid medium, washed and optionally dried. Under the above conditions, the monovalent alkali metal salts of the acids of formula (1) may be typically isolated in hydrated forms, which are preferably crystalline.

If necessary and/or desirable, the isolated crude product is then purified by a suitable process, e.g., by a recrystallization or by an extraction. It may be also converted into another acid/salt/ester form, including any of its hydrated or solvated forms.

The process of the present invention also includes processes for making precursors of the pharmaceutically active biphosphonates, i.e., compounds that would need to undergo a conversion of one group Z to another group Z. In such a case, the above-described process includes a subsequent conversion step (e.g., a step of removing protective groups on certain atoms or a step of further substitution, such as an alkylation, of the original precursor group Z).

The process of the present invention also includes a process for making esters of the acids of the formula (1). For making such esters, the above process may be modified by using esters of phosphorous acid instead of the phosphorous acid in the phosphonation reaction. Alternatively, the esters may be obtained by using an alcohol instead of water in the elaboration of the reaction mixture after the phosphonation reaction, as shown above.

Accordingly, the use of a compound of formula (3) as a solvent/diluent is not limited to the reaction of compounds of formula (2) with a phosphonation agent. In principle, the solvent/diluent of the present invention is useful in any reaction that forms a biphosphonate compound (i.e., any compound having two phosphonic acid residues including esters, salts, etc.) via reaction with a phosphonation agent.

The invention will be further described with reference to the following non-limiting examples.

EXAMPLES

Example 1

Ibandronic Acid in Formaldehyde Diethyl Acetal 3 g of (3-methyl-pentyl-amino)propionic acid hydrochloride 4.46 g of $H_3PO_3$ and 9 ml of ethylal (formaldehyde diethyl acetal) was stirred at 40° C. for 30 minutes. 4.75 ml of $PCl_3$ was added to the reaction mixture during 5 minutes. Reaction mixture was heated to 65° C. and heating continued 5 hours. Then 24 ml of water was added in 10 minutes. Reaction mixture was refluxed at 95° C. of bath temperature for 18 hours. The mixture was cooled to 20° C. and filtered through kieselguhr. The filtered cake was washed with 2 ml of water. The filtrate was neutralized with 5-6 ml of 50% aqueous sodium hydroxide to pH 4.2-4.5. 150 ml of ethanol was added and the mixture was stirred in ice bath for 4 hours. The precipitated crystals were filtered off and washed with 10 ml of ethanol, 10 ml of acetone:water=5:2, 10 ml of acetone, and 10 ml of ether. The crystals were dried at 50° C. Yield: 4.51 g of ibandronic acid sodium salt hydrate.

Example 2

Ibandronic Acid in Formaldehyde Diethyl Acetal 3 g of (3-methyl-pentyl-amino)propionic acid hydrochloride 4.46 g of $H_3PO_3$ and 9 ml of ethylal (formaldehyde diethyl acetal) were stirred at room temperature for 30 minutes. Then 4.75 ml of $PCl_3$ was added during 15 minutes at temperature 22-40° C. The mixture was stirred at 58° C. for 4 hours. Then 24 ml of water was added dropwise and the reaction mixture was stirred at 95° C. (in bath) for 18 hours. Then the mixture was cooled to 20° C. and neutralized with 50% aqueous sodium hydroxide to pH 4.2-4.5 (6 ml). Then 30 ml of ethanol was added and the solution was stirred for 4 hours at 15-20° C. Precipitated crystals were filtered off and washed with 60 ml of mixture (acetone:water=5:2). The crystals were dried at 50° C. Yield: 3.57 g of ibandronic acid sodium salt hydrate.

Example 3

Ibandronic Acid in Formaldehyde Dibutyl Acetal 3 g of (3-methyl-pentyl-amino)propionic acid hydrochloride 4.46 g of $H_3PO_3$ and 9 ml of butylal (Dibutoxymethane) was stirred at 40° C. for 30 minutes. 4.75 ml of $PCl_3$ was added to the reaction mixture during 5 minutes. Reaction mixture was heated to 65° C. for 5 hours. Then 24 ml of water was dropped for 10 minutes. Reaction mixture was refluxed at 95° C. (in bath) for 18 hours. Then mixture was cooled to 20° C. and neutralized with 7-8 ml of 50% aqueous sodium hydroxide to pH 4.2-4.5. 150 ml of ethanol was added and the mixture was stirred in ice bath for 4 hours. The precipitated crystals were filtered off and washed with 10 ml of ethanol, 10 ml of acetone:water=5:2, 10 ml of acetone, and 10 ml of ether. The crystals were dried at 50° C. Yield: 7.94 g of ibandronic acid sodium salt hydrate.

Example 4

Ibandronic acid in 1,3-dioxolan (formaldehyde ethyleneacetal)

3 g of (3-methyl-pentyl-amino)propionic acid hydrochloride 4.46 g of $H_3PO_3$ and 9 ml of 1,3-dioxolan was stirred at 40° C. for 30 minutes. 4.75 ml of $PCl_3$ was added to the reaction mixture during 5 minutes. Reaction mixture was heated to 65° C. for 5 hours. Then 24 ml of water was dropped in 10 minutes. Reaction mixture was heated at 95° C. (in bath) for 18 hours. Then the mixture was cooled to 20° C. and neutralized with 9-10 ml of 50% aqueous sodium hydroxide to pH 4.2-4.5. 150 ml of ethanol was added and the mixture was stirred in ice bath for 4 hours. The precipitated crystals were filtered off and washed with 10 ml of ethanol, 10 ml of acetone:water=5:2, 10 ml of acetone, and 10 ml of ether. The crystals were dried at 50° C. Yield: 7.19 g of ibandronic acid sodium salt hydrate.

Example 5

Ibandronic Acid in Propionaldehyde Diethyl Acetal 3 g of (3-methyl-pentyl-amino)propionic acid hydrochloride 4.46 g of $H_3PO_3$ and 9 ml of propionaldehyde diethyl acetal were stirred at 40° C. for 30 minutes. Then 4.75 ml of $PCl_3$ was added during 5 minutes. Reaction mixture was heated at 65° C. for 4 hours. Then 24 ml of water was added dropwise and the reaction mixture was refluxed at 95° C. (in bath) for 18 hours. The mixture was cooled to 20° C. and filtered with 1 g of kieselguhr. The solution was then neutralized with 9.3 ml of 50% aqueous sodium hydroxide to pH 4.2-4.5 (Mach.-Nagel Tribox). 150 ml of ethanol was added and the solution was stirred on ice bath for 2 hours. The solution was stored at −15° C. for 18 h. The precipitated crystals were filtered off and washed with 9.0 ml of ethanol 9.0 ml of acetone:water=5:2, 9.0 ml of acetone, and 9.0 ml of ether. The crystals were dried at 50° C. Yield: 2.17 g of ibandronic acid sodium salt hydrate.

Example 6

Ibandronic Acid in Trimethyl Orthoformate 3 g of (3-methyl-pentyl-amino)propionic acid hydrochloride 4.46 g of $H_3PO_3$ and 9 ml of trimethyl orthoformate were stirred at 40° C. for 30 minutes. Then 4.75 ml of $PCl_3$ was added during 5 minutes. Reaction mixture (yellow oil) was heated at 65° C. for 4 hours. Then 24 ml of water was added dropwise and the reaction mixture was heated at 95° C. (in bath) for 19 hours. The yellow mixture was cooled to 20° C. and filtered with 1 g of kieselguhr. The solution was then neutralized with 9.3 ml of 50% aqueous sodium hydroxide to pH 4.2-4.5 (Mach.-Nagel Tribox). 150 ml of ethanol was added and the solution was stirred on ice bath for 2 hours. The solution was stored at −15° C. for 18 h. The precipitated crystals were filtered off and washed with 15 ml of ethanol, 15 ml of acetone:water=5:2, 15 ml of acetone, and 15 ml of ether. The crystals were dried at 50° C. Yield: 2.74 g of ibandronic acid sodium salt hydrate.

Example 7

Ibandronic Acid in Triethyl Orthoacetate 3 g of (3-methyl-pentyl-amino)propionic acid hydrochloride 4.46 g of $H_3PO_3$ and 9 ml of triethylorthoacetate was stirred at 40° C. for 30 minutes. 4.75 ml of $PCl_3$ was added to the solution during 5 minutes. Reaction mixture was heated to 58° C. for 5 hours. Then 24 ml of water was added in 10 minutes and the reaction mixture was refluxed at 95° C. (in bath) for 18 hours. Then the mixture was cooled to 20° C. and filtered through kieselguhr. The filtered cake was washed with 2 ml of water. The filtrate was neutralized with 7-8 ml of 50% aqueous sodium hydroxide to pH 4.2-4.5. 150 ml of ethanol was added and the mixture was stirred in ice bath for 2 hours. The precipitated crystals were filtered off and washed with 10 ml of ethanol, 10 ml of acetone:water=5:2, 10 ml of acetone, and 10 ml of ether. The crystals were dried at 50° C. Yield: 5.29 g of ibandronic acid sodium salt hydrate.

Example 8

Ibandronic Acid in Formaldehyde Diethyl Acetal 3 g of (3-methyl-pentyl-amino) propionic acid hydrochloride 4.46 g of $H_3PO_3$ and 9 ml of ethylal (formaldehyde diethyl acetal) was stirred at 40° C. for 30 minutes. 4.75 ml of $PCl_3$ was added to the reaction mixture during 5 minutes. Reaction mixture was heated to 58° C. and heating continued 5 hours. Then 29 ml of methanol was added to the reaction mixture. Reaction mixture was heated for 1 hour at reflux and then the solvents were distilled off. 9 ml of toluene was added and distilled off and again 9 ml of toluene was added and distilled off. 24 ml of water was added into the residue and the solution was stirred for 18 hour at 95° C. (in bath). Then the mixture was cooled to 20° C. and neutralized with 5-6 ml of 50% aqueous sodium hydroxide to pH 4.2-4.5. 150 ml of ethanol was added into light solution and it was stirred in ice bath for 2 hours. The precipitated crystals were filtered off and washed with 10 ml of ethanol, 10 ml of acetone:water=5: 2, 10 ml of acetone, and 10 ml of ether. The crystals were dried at 50° C. Yield: 1.11 g of the ibandronic acid monohydrate (first crop).

The filtrate was stirred overnight. The precipitated crystals were filtered off and washed with 10 ml of ethanol, 10 ml of acetone:water=5:2, 10 ml of acetone, and 10 ml of ether. The crystals were dried at 50° C. Yield: 0.94 g of the ibandronic acid monohydrate (second crop).

Each of the patents and patent applications mentioned above are incorporated herein by reference. The invention having been described it will be obvious that the same may be varied in many ways and all such modifications are contemplated as being within the scope of the invention as defined by the following claims.

I claim:
1. A process of making a biphosphonate, which comprises:
    reacting in a solvent/diluent a carboxylic acid compound of formula (2) or a salt thereof

Z—COOH     (2), wherein Z represents a C1-C6 alkyl group optionally substituted by an amino group, one or two C1-C6 alkylamino group(s), or a nitrogen-containing heterocyclic group, with a phosphonation agent to form cyclic pyrophosphonate intermediates, wherein said solvent/diluent comprises at least one compound of formula (3)

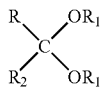
(3)

wherein R is hydrogen or a C1-C6 alkyl group; each of R1 is a C1-C6 alkyl group or both R1 groups are linked to form a C1-C3 alkylene group; and R2 is hydrogen, a C1-C6 alkyl group, a C1-C6 alkoxy group, or is linked together with R to form a C3-C7 carbon ring; and hydrolyzing said cyclic pyrophosphonate intermediates to form a compound of formula (1) or a salt or hydrate thereof

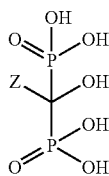
(1)

wherein Z is as defined above.

2. The process according to the claim 1, wherein R2 in the compound of formula (3) is hydrogen.

3. The process according to claim 2, wherein R and R2 are hydrogen and R1 represents a C1-C6 alkyl group.

4. The process according to claim 3, wherein the compound of formula (3) is formaldehyde diethyl acetal.

5. The process according to claim 1, wherein Z is selected from the group consisting of methyl, 2-aminoethyl, 3-aminopropyl, 5-aminopentyl, 2-(N,N-dimethylamino)ethyl, 2-(N-methyl-N-pentylamino)ethyl, pyridin-3-ylmethyl, 2-imidazol-1-ylmethyl, and (imidazo[1,2a]pyridin-2-yl)methyl.

6. The process according to claim 1, wherein said solvent/diluent further comprises an inert co-solvent.

7. The process according to claim 1, wherein said solvent/diluent comprising said compound of formula (3) is used in an amount of 2 to 10 volumes based on the weight of the compound of formula (2).

8. The process according to claim 1, wherein said phosphonation agent comprises a halophosphorous compound selected from the group consisting of phosphorous trichloride $PCl_3$, phosphorous pentachloride $PCl_5$, and phosphorous oxychloride $POCl_3$.

9. The process according to claim 1, wherein said phosphonation agent comprises phosphorous acid and a halophosphorous compound.

10. The process according to claim 9, wherein a molar ratio between said compound of formula (2), said phosphorous acid, and said halophosphorous compound is about 1: (1-5): (2-5).

11. The process according to claim 1, wherein said hydrolyzing step comprises contacting, under reactive conditions, said cyclic pyrophosphonate intermediates with water, alcohol, or a mixture thereof.

12. The process according to claim 11, which further comprises isolating said compound of formula (1) or a salt or hydrate thereof from the reaction mixture by precipitation.

13. In a process of making biphosphonate compounds by reacting an acid or ester with a phosphonation agent, the improvement for which comprises carrying out said reaction in a solvent/diluent that comprises a compound of formula (3)

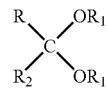
(3)

wherein R is hydrogen or a C1-C6 alkyl group; each of R1 is a C1-C6 alkyl group or both R1 groups are linked to form a C1-C3 alkylene group; and R2 is hydrogen, a C1-C6 alkyl group, a C1-C6 alkoxy group, or is linked together with R to form a C3-C7 carbon ring.

* * * * *